United States Patent

Aoki et al.

[11] Patent Number: 5,766,247
[45] Date of Patent: Jun. 16, 1998

[54] PROCESS FOR PRODUCING A BIOIMBEDDING MATERIAL

[75] Inventors: Hideki Aoki, Inashiki-gun; Yoshiharu Shin, Higashimurayama; Kazutake Yoshizawa, Tokyo; Takahiro Iida, Tokorozawa, all of Japan

[73] Assignee: Kabushiki Kaisya Advance, Tokyo, Japan

[21] Appl. No.: 501,041

[22] PCT Filed: Dec. 8, 1994

[86] PCT No.: PCT/JP94/02066

§ 371 Date: Aug. 9, 1995

§ 102(e) Date: Aug. 9, 1995

[87] PCT Pub. No.: WO95/15775

PCT Pub. Date: Jun. 15, 1995

[30] Foreign Application Priority Data

Dec. 10, 1993 [JP] Japan ................. 5-340914

[51] Int. Cl.⁶ ............................... A61F 2/02
[52] U.S. Cl. ............... 623/11; 623/16; 623/18; 623/66; 523/1; 523/105; 523/115
[58] Field of Search .............. 623/1, 7–8, 11, 623/13, 16–23, 66; 523/1, 105–111, 112–115

[56] References Cited

U.S. PATENT DOCUMENTS

| 4,846,838 | 7/1989 | Takai et al. ..................... 623/16 |
| 5,073,373 | 12/1991 | O'Leary et al. ................. 623/16 |
| 5,178,845 | 1/1993 | Constantl et al. .............. 423/305 |
| 5,376,375 | 12/1994 | Rhee et al. ..................... 424/423 |

FOREIGN PATENT DOCUMENTS

| 0 276 836 | 8/1988 | European Pat. Off. . |
| 63-153072 | 6/1988 | Japan . |
| 1-268560 | 10/1989 | Japan . |
| 2-51475 | 2/1990 | Japan . |
| 3-82474 | 4/1991 | Japan . |

Primary Examiner—John G. Weiss
Assistant Examiner—Francis K. Cuddihy
Attorney, Agent, or Firm—Finnegan, Henderson, Farabow, Garrett & Dunner, L.L.P.

[57] ABSTRACT

A bioimbedding material comprising a mixture of ultrafine hydroxyapatite powder having a particle size of 2 µm or less, and a polymer or oligomer, which can function as a tissue substitute for a long time in a living organism, without causing inflammation, which has flexibility and elasticity, which has an excellent biocompatibility and contrast, and which does not require a contrast line, and a process for producing the same.

3 Claims, 2 Drawing Sheets

1

PROCESS FOR PRODUCING A BIOIMBEDDING MATERIAL

TECHNICAL FIELD

The present invention relates to bioimbedding materials and a process for producing the same.

BACKGROUND ART

Generally, as a material for applying to a soft tissue in a living organism (or body) or as a material for a catheter, etc., several kinds of polymers are used. These materials, however, are foreign to the living organism. Particularly, in the case of a catheter, etc. connecting the outside and inside of the living organism, bacteria is likely to enter the living organism through the opening in the skin so that inflammation or infection may easily occur. Thus, these materials cannot be used for a long time.

A contrast line, using a contrast medium such as barium sulfate or tungsten oxide and imbedded in a catheter, etc., may cause a breakage of the catheter along the contrast line, which is an uncertain factor from the viewpoints of strength. Further, a material to which a contrast medium is directly inserted may cause harm to a living organism due to the release of the contrast medium.

Hydroxyapatite is known to have an excellent biocompatibility and, therefore, is clinically used as, for example, artificial bones. However, since hydroxyapatite is extremely hard, compared to living tissue, and lacks elasticity and flexibility, hydroxyapatite is unsuitable as a material such as catheter for applying to a soft material.

DISCLOSURE OF INVENTION

In view of the state of the above-described prior art, the object of the present invention is to provide a bioimbedding material which does not cause inflammation and can function for a long time in the living organism, which has flexibility and elasticity and, further, has an excellent biocompatibility and contrastability, without requiring a contrast line.

In accordance with the present invention, there is provided a bioimbedding material comprising a mixture of ultrafine hydroxyapatite powder having a particle diameter of 2 μm or less, and a polymer or oligomer.

In accordance with the present invention, there is also provided a process for producing a bioimbedding material comprising drying or thermally treating hydroxyapatite obtained by wet synthesis to form the ultrafine powder thereof, followed by mixing with a polymer or oligomer.

BRIEF DESCRIPTION OF DRAWINGS

The present invention will now be explained in detail below with reference to the drawings.

FIG. 1 represents the change in the tensile strength and the tearing strength of silicone rubber corresponding to the addition amount of hydroxyapatite (HA), and FIG. 2 represents the change in the thickness of a fibrous film formed around a sample.

BEST MODE FOR CARRYING OUT THE INVENTION

Figure 1:
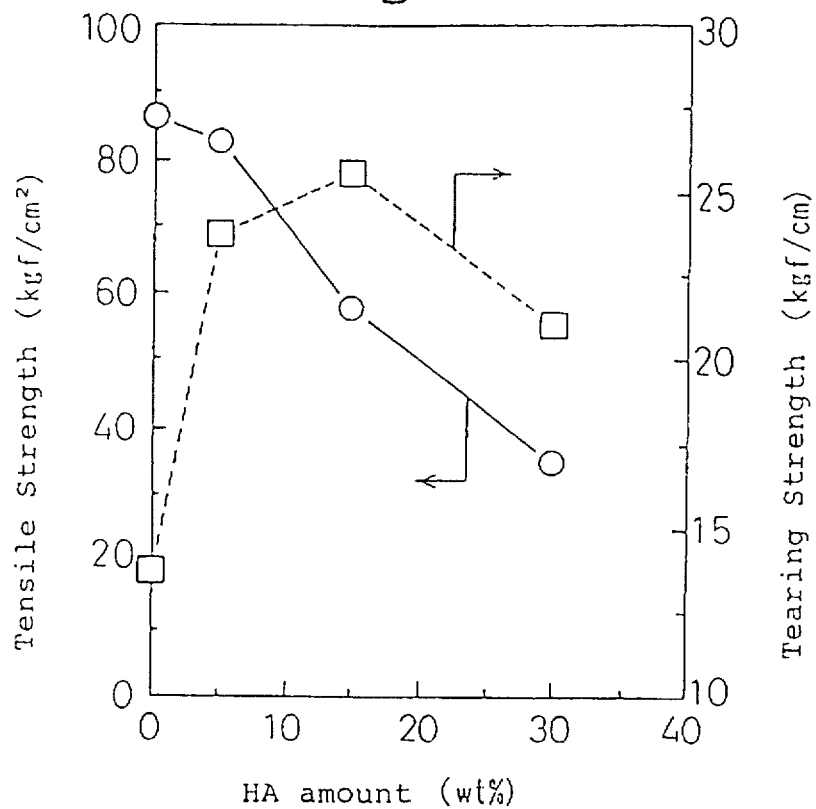
FIGS. 1 and 2, are graphs representing the results of Example 1.

The composition, the shape or the structure and the embodiment of use of the bioimbedding material according to the present invention will be individually described, in detail, below.

Composition of and Production Method for the Material

"Hydroxyapatite" used in the present invention may include not only the pure product represented by $Ca_{10}(PO_4)_6(OH)_2$ in terms of the chemical composition, but also those further comprising 1–10% of a carbonate ($CO_3$) ion, fluorine or chlorine ion, etc., instead of the OH ion. The hydroxyapatite of the present invention may also include those mainly containing the above-mentioned compounds and, additionally, to improve the sintering ability, strength, porosity, etc., may include well known various additives such as $Ca_3(PO_4)_2$, MgO, $Na_2O$, $K_2O$, $CaF_2$, $Al_2O_3$, $SiO_2$, CaO, $Fe_2O_3$, $MnO_2$, ZnO, C, SrO, PbO, BaO, $TiO_2$, $ZrO_2$ added thereto or mixed therewith.

The hydroxyapatite having the above-mentioned components means those having a mole ratio of Ca/P of 1.67. However, calcium phosphates alone such as deficient apatite, tricalcium phosphate, tetracalcium phosphate and octacalcium phosphate, or composite products comprising two or more of these compounds have substantially the equivalent function to those of the hydroxyapatite.

Fine hydroxyapatite powder is obtained by dropwise adding an aqueous phosphoric acid to a stirred 0.5M calcium hydroxide suspension to cause a uniform reaction to thereby obtain an amorphous hydroxyapatite suspension, then filtering and drying the same at 60° C., followed by milling by means of an ultrafine milling apparatus such as a jet mill. The resulting ultrafine hydroxyapatite powder is dried and the foaming resulting from the water-evaporation at the time of kneading with a polymer or of molding at 150°–350° C. is thus eliminated, whereby a uniform composite material can be produced. At this point, the fine powder is converted to a low crystalline hydroxyapatite and the primary particle size thereof is several hundreds angstroms. Although the agglomerated secondary particles have a particle size of about 2 μm, they are readily ruptured during an adequate kneading process, with a polymer by means of a kneader, emulsifier, homogenizer, etc. The dispersion of particles having size of several hundreds angstroms has the effect of suppressing the strength reduction in the composite material as little as possible and the addition of a coupling agent, as used with larger particles in view of the bonding force or adhesion with the matrix polymer, is not necessary. Even if the release or dissolution of the particles from the composite material into a living tissue occurs, the particle size is much smaller than that of cells which have an average size of 1 μm. Thus, the foreign body reaction or phagocytosis by cells caused by the particles is small. Further, the hydroxyapatite has a higher dissolution rate than that of high crystalline hydroxyapatite, whereby it can exhibit effects for enhancing a biocompatibility at earlier stages.

When hydroxyapatite is baked at a temperature of 800° C. or more, it has a high crystallinity and, at the same time, the outside of the particles begins to calcine so that the growth of the particles proceeds. Accordingly, the problems described above are revealed, the strength of the composite material decreases and the tissue response is inferior even to materials having no hydroxyapatite.

It has been conventionally known that hydroxyapatite crystal begins to grow at about 700° C. or more and that, when the thermal treatment is carried out at 700° C. or less and it is imbedded, the tissue reaction is poor, for example, foreign matter in the form of macro molecules appear, and that a thermal treatment at 800° C. to 900° C. gives a product having the most preferable biocompatibility. However, according to animal experiment results conducted by the inventors, it was found that a silicone rubber composite material which was mixed with hydroxyapatite powder thermally treated at 800° C. could induce the invasion of inflammatory cells compared with a silicone rubber, without the hydroxyapatite powder, to thereby worsen the tissue response.

Further, a silicone based oligomer has been used as a cosmetic surgical tissue filler, for example, for artificial breasts. The silicone type oligomer may cause a strong inflammatory tissue reaction so that the surrounding soft tissue may be extremely thickened to cause various problems such as a dull pain.

The hydroxyapatite usable according to the present invention is preferably in the form of ultrafine particles. In the thermal growth at a high temperature, during the production of the hydroxyapatite of the present invention, since particles are grown by the crystallization thereof, the particles are dried at a temperature as low as possible for a short time, followed by milling with ultrafine milling apparatus etc. to suppress the agglomeration. Thus, an ideal composite material having a suppressed strength decrease of the matrix and exhibiting a biocompatibility of hydroxyapatite can be proposed. Further, by employing such low temperatures, the cost required for the facilities can be reduced.

As to the drying conditions, drying at a temperature of 200° C. or less is desirable for suppressing the growth and agglomeration of particles. The employment of drying such as freeze-drying or vacuum drying is further effective.

In order to accelerate the above-mentioned drying, a thermal treatment at about 400° C. can be effected, but at such temperature, the growth and agglomeration of particles inevitably occur. In such a case, a rather desirable composite material can be obtained by making the particles size, before the thermal treatment, 5 μm or less.

By adding the above-mentioned ultrafine hydroxyapatite particles having a particle diameter of 2 μm or less in an amount of 5–30% by weight, on the basis of the weight of the matrix, followed by uniformly and sufficiently mixing to obtain a composite material, the tissue reaction can be noticeably decreased, while sufficiently maintaining the characteristics of a matrix polymer or oligomer.

The above-mentioned polymer can be selected, for example, from polyethylene, polypropylene, polymethyl methacrylate, polyurethane, polyester, acrylonitrile-butadiene-styrene resins, polycarbonate, polysulfone, epoxy resins, silicone resins, diacryl phthalate resins and furan resins. These resins may further include a reinforcing material such as C, SiC, $SiO_2$, $Al_2O_3$, $ZrO_2$, $TiO_2$, W, Mo, stainless steel, titanium metal, and other fillers.

The typical examples of the oligomer are silicone, but the oligomer can be the oligomers of the above-mentioned other high molecular weight materials.

EXAMPLES

The present invention is further described in detail by way of, but is by no means limited to, the following Examples.

Example 1

Hydroxyapatite ultrafine powder having a particle size of 5 μm or less and obtained by wet-synthesis, was dried for one night at 400° C. and the resulting dried powder was mixed with an addition-type silicon rubber compound in an amount of 5, 15 and 30% by weight. The compounds were sufficiently kneaded and then molded into a sheet having a thickness of 2 mm. Thereafter, secondary vulcanization was effected.

Physical Property Test

The product was cut to an intended shape. Then, a physical property test thereof was conducted according to JIS (i.e., Japanese Industrial Standard) standard vulcanized rubber physical test method K 6301.

The tensile strength values were 86, 83, 58 and 35 $kgf/cm^2$, corresponding to addition amounts of the hydroxyapatite of 0, 5, 15 and 30% by weight, respectively. That is, the tensile strength was decreased in proportion to the addition amount of the hydroxyapatite. On the contrary, the hardness values were 69, 71, 75, 80, that is, the hardness increased in proportion to the addition amount.

The tearing strength values were 14, 24, 26, 21 $kgf/cm^2$, respectively. Thus, it was observed that the tearing strength increased with the addition of the hydroxyapatite and had the maximum value at around 15% by weight of the addition amount (FIG. 1).

Animal Test

Samples of each material, having the size of 15 mm×15 mm and comprising 0, 5, 15, 30% by weight of the hydroxyapatite, respectively, were subcutaneously imbedded into dogs. At two weeks, and at 1, 3, and 6 months after the imbedding, the imbedded material was extracted together with the surrounding tissue and a pathological tissue preparation was made and observed through a light microscope.

It was observed that the fibrous film formed around a composite material comprising hydroxyapatite was thin compared with the film formed around silicone without hydroxyapatite, and the tissue reaction was usually small.

Figure 2:
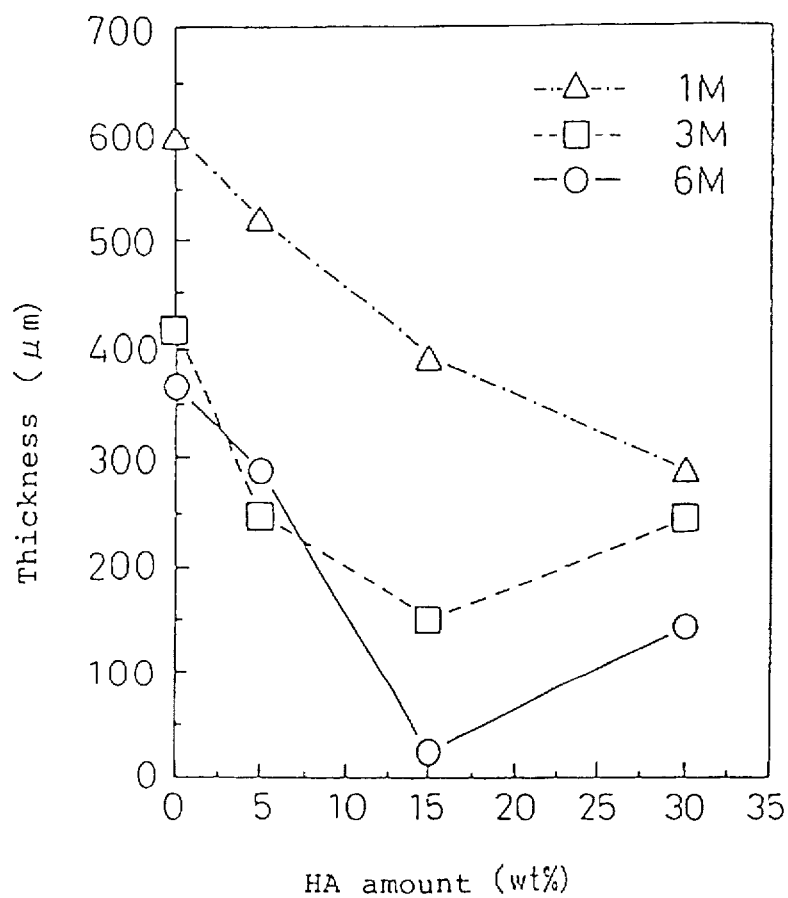

The thickness of the film around the composite material at six months after insertion was about 365, 290, 25 and 150 μm, corresponding to a hydroxyapatite amounts of 0, 5, 15 and 30% by weight, respectively. At a hydroxyapatite amount of 15% by weight, the surrounding film was observed to have the minimum thickness (FIG. 2).

Example 2

Samples of hydroxyapatite, obtained according to the wet synthesis, was thermally treated at 60° C., 400° C. or 800° C. for 2 hours, and the specific surface area of the treated products was measured by means of BETT-type specific surface area meter.

As a result, it was found that the specific surface area of the product thermally treated at 60° C. was about 95 $m^2/g$, it was about 50 $m^2/g$ when treated at 400° C., and it was about 15 $m^2/g$ when treated at 800° C. From these results, it could be seen that the drying at a low temperature can increase the specific surface area, i.e., can suppress the growth of particles which may occur concomitant with the crystallization and agglomeration of particles.

Example 3

Samples of hydroxyapatite obtained according to wet synthesis were thermally treated at 60° C., 400° C. or 800° C., for 2 hours to obtain ultrafine powder of hydroxyapatite. Each ultrafine hydroxyapatite powder was mixed with silicone rubber compound in an amount of 15% by weight, then each resulting mixture was subjected to a tensile strength test.

As the result, each tensile strength was 65, 58 and 48 $kgf/cm^2$, respectively. Thus, it could be seen that the tensile strength decreased with an increase in the heating temperature.

INDUSTRIAL APPLICABILITY

As mentioned above, the present invention has effects of functioning as a tissue substitute for a long time and preventing inflammation in the living organism, has flexibility and elasticity, and further has an excellent biocompatibility and X ray contrast without requiring a contrast line.

We claim:

1. A process for producing a bioimbedding composite material comprising drying hydroxyapatite obtained by wet synthesis at 200° C. or less and then thermally treating the dried hydroxyapatite at 400° C. or less to form an ultrafine powder thereof having a particle size of 2 μm or less, followed by mixing from 5 to 30% by weight, based upon the total material, of the ultrafine hydroxyapatite powder with a polymer or oligomer.

2. The process for producing a bioimbedding composite material as claimed in claim 1, wherein the particle size of the hydroxyapatite before the thermal treatment is 5 μm or less.

3. The process for producing a bioimbedding composite material as claimed in claim 1, wherein said polymer or oligomer is selected from the group consisting of the polymers or oligomers of ethylene, propylene, methyl methacrylate, urethane, ester, acrylonitrile-butadiene-styrene, carbonate, sulfone, epoxy, silicone, diacryl phthalate and furan.

* * * * *